United States Patent [19]

Faler

[11] 4,396,728

[45] Aug. 2, 1983

[54] METHOD AND CATALYST FOR MAKING BISPHENOL

[75] Inventor: Gary R. Faler, Scotia, N.Y.

[73] Assignee: General Electric Company, Schenectady, N.Y.

[21] Appl. No.: 298,711

[22] Filed: Sep. 2, 1981

Related U.S. Application Data

[63] Continuation-in-part of Ser. No. 192,447, Sep. 30, 1980, abandoned.

[51] Int. Cl.$^3$ .................... B01J 31/00; C07C 37/00
[52] U.S. Cl. .................................. 521/32; 568/728
[58] Field of Search ................ 521/32, 28; 568/728

[56] References Cited

FOREIGN PATENT DOCUMENTS 23325  7/1979  European Pat. Off. .
2931036  7/1979  Fed. Rep. of Germany .

Primary Examiner—Joseph L. Schofer
Assistant Examiner—Peter F. Kulkosky
Attorney, Agent, or Firm—William A. Teoli; James C. Davis, Jr.; James Magee, Jr.

[57] ABSTRACT

A sulfonated aromatic organic polymer, such as sulfonated polystyrene ion-exchange resin, is provided having N-alkylaminoorgano mercaptan groups attached to backbone sulfonyl radicals by covalent nitrogen-sulfur linkages. The ion-exchange resin can be used to effect phenol-ketone condensation in the synthesis of bisphenols.

8 Claims, No Drawings

METHOD AND CATALYST FOR MAKING BISPHENOL

CROSS REFERENCE TO RELATED APPLICATIONS

This application is a continuation-in-part of copending application Ser. No. 192,447, filed Sept. 30, 1980 and now abandoned. Reference also is made to copending applications of Faler et al, Ser. No. 103,095, filed Dec. 13, 1979, for Method and Catalyst for Making Bisphenols mow U.S. Pat. No. 4,294,995 and Ser. No. 252,493, filed Apr. 8, 1981 and now abandoned, and Ser. No. 226,271, filed Jan. 19, 1981, for Method for Salvaging Bisphenol Values, of Ashok Mandiratta, where all of the aforementioned applications are assigned to the same assignee as the present invention.

BACKGROUND OF THE INVENTION

Prior to the present invention, various methods were employed to synthesize bisphenols, such as bisphenol-A, by effecting reaction between a ketone and a phenol. One procedure, for example, involved the use of large amounts of inorganic acid catalysts, such as sulfuric acid or hydrochloric acid. Experience has shown, however, that the use of inorganic acids requires a means to neutralize such acids at the end of the reaction due to the corrosive action of the strong acids. In addition, distillation of the resulting bisphenol is often required because of the many by-products formed during the reaction under high acid conditions.

An improved procedure was developed by using a solid resin cation-exchange catalyst to effect the condensation between the phenol and the ketone. However, the disadvantage of the ion-exchange catalyst is the low acid concentration it provides resulting in the need for a rate accelerator such as a mercaptan. One procedure is shown by Apel et al, U.S. Pat. No. 3,153,001, which incorporates the mercaptan by partial esterification of the ion-exchange catalyst in the form of a sulfonated insoluble polystyrene resin. Another procedure involves the partial neutralization of such sulfonic acid moiety with an alkyl mercapto amine, as shown by McNutt et al, U.S. Pat. No. 3,394,089. A further procedure is shown by Wagner et al, U.S. Pat. No. 3,172,916, based on the partial reduction of the sulfonic acid to afford thiophenol functional groups. It has been found, however, that Wagner et al does not afford a particularly active type of promoter for synthesizing bisphenols, such as bisphenol-A. The methods of Apel et al and McNutt et al are also unsatisfactory after extended use under continuous reaction conditions, since the ion-exchange resins used in these methods readily lose mercaptan when attempts are made to regenerate them.

In copending application Ser. No. 103,095, filed Dec. 13, 1979 there is taught that N-organoaminodisulfide of the formula,

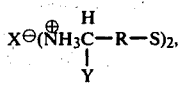

where X is a halogen radical or a counter ion, such as sulfate, Y is selected from hydrogen, carboxy and nitrile and R is a $C_{(1-13)}$ divalent organic radical selected from aliphatic and aromatic radicals, can be used to incorporate covalently bonded organo mercaptan groups into the backbone of the sulfonated aromatic organic polymer. Although improved results were obtained by using such ion-exchange resin to form bisphenols from phenol and acetone as compared to the aforementioned resins of the prior art, it was found that the use of such catalyst to form bisphenol from acetone and phenol under continuous reaction conditions resulted in a gradual reduction in the percent conversion of bisphenol during the course of the reaction.

The present invention is based on the discovery that N-alkylaminoorgano disulfide of the formula,

can be used to produce sulfonated aromatic organic polymer containing N-alkylaminoorgano mercaptan groups attached to backbone sulfonyl radicals by covalent nitrogen-sulfur linkages, exhibiting substantially enhanced stability under continuous reaction conditions during the production of bisphenol from a ketone and phenol without a significant reduction in rate of bisphenol formation as compared to the aforementioned ion-exchange resin provided by the copending application Ser. No. 103,095 as described above, where $R^1$ is a $C_{(1-8)}$ monovalent alkyl radical and R, X and Y are as previously defined.

It has been found that after chemical attachment of the N-alkylaminoorgano disulfide of formula (1) to the polymer backbone as defined below, it can be reduced with a triorganophosphine, whereby the disulfide is converted to a mercaptan after acidification.

STATEMENT OF THE INVENTION

There is provided by the present invention, an ion-exchange resin comprising a sulfonated polyaromatic organic material having from about 5 to about 40 mole percent, and preferably 10 to 30 of sulfonated aromatic organic mercaptan units of the formula,

chemically combined with from about 60 to about 95 mole percent of mercaptan-free organic units selected from

and

and combinations of such chemically combined mercaptan-free organic units, which sulfonated polyaromatic organic material is selected from (A) aromatic organic polymer having from about 5 to about 40 mole percent of said sulfonated aromatic organic mercaptan units chemically combined with from about 60 mole percent to about 95 mole percent of said mercaptan-free organic units and (B) a blend of (i) aromatic organic polymer having at least about 10 mole percent of the sulfonated aromatic organic N-alkylaminoorgano mercaptan units of formula (2) chemically combined with up to 90 mole percent of the mercaptan-free organic units of formulas (3) and 4, where the total sum of chemically combined units is 100 mole percent, and (ii) a sulfonated aromatic organic polymer consisting essentially of the chemically combined mercaptan-free organic units of formulas (3) and (4), where R, $R^1$ and Y are as previously defined, $R^2$ is a trivalent $C_{(6-13)}$ aromatic organic radical, $R^3$ is a divalent $C_{(6-13)}$ aromatic organic radical.

A further aspect of the present invention is directed to a method of making an aromatic organic polymer having N-alkylaminoorgano mercaptan groups attached to backbone sulfonyl radicals by covalent sulfur linkages hereinafter referred to as sulfonated aromatic organic polymer containing N-alkylaminoorgano mercaptan groups which comprises, (C) effecting reaction between
 (a) a halosulfonated aromatic organic polymer, and
 (b) an N-alkylaminoorgano disulfide of formula (1) in the presence of base, (D) treating the resulting mixture of (C) with an effective amount of a tri-organo phosphine which is sufficient to convert the resulting disulfide adduct to a mercaptan unit of formula (2) and (E) recovering the resulting aromatic organic polymer having chemically combined units of formula (2).

Halosulfonated aromatic organic polymer which can be halosulfonated and utilized in the practice of the method of the present invention consists essentially of from about 5 to 95 mole percent of sulfonated aromatic organic units of formula (3), chemically combined with from about 95 mole percent of 5 mole percent of $C_{(6-13)}$ aromatic organic units of formula (4).

In a further aspect of the present invention, there is provided a method for making bisphenol, which prior to the present invention, was based on the reaction between a ketone and a phenol in the presence of an effective amount of cation-exchange resin having from 5–25 mole percent of chemically combined divalent units of the formula,

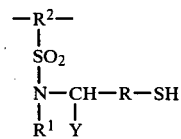

whereby the rate of bisphenol formation gradually reduced under continuous reaction conditions, the improvement which comprises utilizing as the cation-exchange resin, an insoluble ion-exchange material having 5–40 mole percent of chemically combined units of formula (2), whereby the rate of formation of bisphenol from the condensation of ketone and phenol under continous conditions is maintained.

There are included by the divalent $C_{(1-13)}$ organo radicals of R of formulas 1 and 2, alkylene radicals, for example, methylene, ethylene, propylene, butylene, pentylene, etc.; aromatic radicals, for example, phenylene, xylylene, tolylene, naphthylene, etc. In addition, R also includes substituted alkylene and arylene radicals as previously defined, such as holo-substituted, for example, chloro, fluoro, etc. Included within the radicals of $R^2$ and $R^3$ are, for example, divalent radicals and trivalent radicals such as

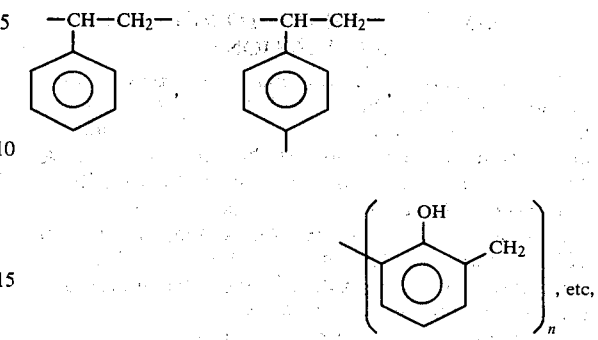

where n is at least one.

Phenols which can be used in the practice of the present invention in the above-identified method for making bisphenols are, for example, phenol and substituted phenols, such as

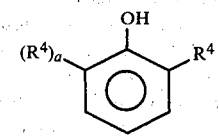

where $R^4$ is selected from $R^1$ radicals, for example, methyl, ethyl, etc., and a is equal to 0 or 1.

Typical of the triorganophosphines which can be used in the practice of the invention are, for example, $$(R^5)_3P \qquad (5)$$

where $R^5$ is selected from a $C_{(4-8)}$ alkyl radical or $C_{(6-13)}$ aryl radical. Some of the triorganophosphines included within formula (5) are, for example, tri-n-butyl phosphine, triphenylphosphine, etc.

Ketones which can be employed in the practice of the present invention to make the aforementioned bisphenols are, for example, acetone, diethyl ketone, methylethyl ketone, cyclohexanone, etc.

Sulfonated aromatic organic polymers having formula (3) and formula (4) units which can be halosulfonated and modified in accordance with the practice of the present invention with N-alkylaminoorgano disulfide of formula (1) are, for example, Amberlite-118, manufactured by Rohm and Haas Company, Dowex 50W X4, manufactured by Dow Chemical Company, etc., and other sulfonated polystyrenes which have been crosslinked with divinylbenzene.

The modification of the above-described ion-exchange resin with the N-alkylaminoorgano disulfide of formula (1) can be accomplished in accordance with the following reaction:

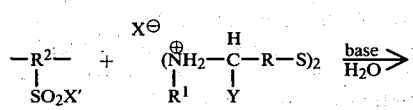

-continued

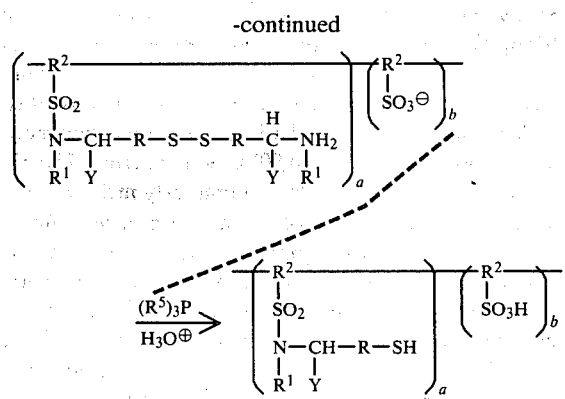

where R, $R^1$, $R^2$, $R^5$, X, and Y are as previously defined X' is halogen and a and b are mole percent ranges within the scope of the present invention.

In the preparation of the sulfonated aromatic organic polymer containing N-alkylorgano mercaptan groups, the halosulfonated aromatic organic polymer can be contacted with N-alkylaminoorgano disulfide of formula (1) in the presence of a suitable solvent and a base to produce a disulfide derivative of the sulfonated aromatic organic polymer. Suitable solvents which can be used, for example, are water, methanol, ethanol, etc. Bases which can be used in the formation of the disulfide adduct are tertiary organic amines such as triethylamine, pyridine, 4-(N-dimethyl amino)-pyridine, trimethylamine, etc. The proportions of the N-alkylaminoorgano disuflide of formula (1) which can be employed will depend on the mole percent substitution of the halosulfonyl radicals on the backbone of the aromatic organic polymer. It has been found that effective results can be achieved if sufficient formula (1) disulfide is employed to provide at least 0.1 to 2 equivalents of nitrogen per equivalent of halosulfonyl of the ion-exchange resin. Temperatures during the addition reaction can be 50° to 100° C. along with a sufficient agitation to facilitate reaction. If desired, an alkali metal carbonate or bicarbonate, such as sodium bicarbonate, can be employed as the base in place of the tertiary organic amine which would simultaneously effect the reaction while neutralizing the excess unreacted halogen on the halosulfonyl radicals.

The reduction of the disulfide derivative of the sulfonated aromatic organic polymer can be achieved by the use of a triorganophosphine by mixing the adduct with the triorganophosphine. A preferred procedure is to add the triorganophosphine in the form of an organic solvent solution to a mixture of the disulfide adduct in an aqueous organic solvent mixture. The resulting mixture can thereafter be stirred under ambient conditions or heated for several hours. The resulting reaction mixture can then be filtered and the recovered ion-exchange resin reaction product can be washed with an alkanol such as methanol, a suitable organic solvent, for example, methylene chloride, and further washed with aqueous hydrochloric acid solution followed by additional washing with organic solvent such methanol, acetone, etc., followed by drying the resulting product in a drying oven at a temperature in the range of from 50° C. to 110° C.

An additional method for making the sulfonated aromatic organic polymer having N-alkylorgano mercaptan groups of the present invention is, for example, the reaction of an appropriate chloroamine, such as N-methyl-2-chloroethyl amine with chlorosulfonated aromatic organic polymer with subsequent treatment of the resulting product with an alkali metal sulfide and triorganophosphine.

Further methods involve the reaction of the resulting product of reaction of N-methyl-2-chloroethylamine and chlorosulfonated aromatic organic polymer with thiourea or a xanthate followed by base treatment, an alkali thiocyanate followed by amine treatment or a tert-butyl mercaptan followed by acid treatment in place of the above-described alkali metal sulfide and triorganophosphine, etc.

Analysis of the resulting sulfonated aromatic organic polymer containing N-alkylaminoorgano mercaptan groups can be determined by titration of the residual sulfonic acid with excess 0.1 N NaOh, followed by back titration of the remaining NaOH with 0.1 N HCl. This procedure provides the acid milliequivalency of the acid catalyst. The amount of nitrogen present on the catalyst can be obtained by combustion analysis which is an indirect estimate of the mercaptan content of the catalyst.

With respect to the preparation of bisphenols utilizing sulfonated aromatic organic polymer containing N-alkylaminoorgano mercaptan groups of the present invention, a mixture of phenol and ketone can be heated in the presence of the cation-exchange resin prepared in accordance with the practice of the present invention. There can be utilized about 2 moles of the phenol per mole of the ketone which can be heated at a temperature in the range of from 50° C. to 110° C. with agitation. The ion-exchange resin can be employed at from 0.1% to 10% by weight, based on the weight of the total mixture in instances where a batch process is used. In a preferred procedure for making bisphenol in a continuous manner, the ion-exchange resin can be used in a column which can be operated at a temperature of 50° C. to 100° C. The mole ratio of reactants can vary widely, such as from about 3 to 1 to about 20 to 1 moles of phenol to ketone. It is preferred, however, to use the reactants at a mole ratio of about 4 to 1 to about 12 to 1 moles of phenol to ketone.

One method of recovering the bisphenol reaction product, for example Bisphenol-A, is by crystallizing the BPA/phenol adduct from the reactor effluent and recovery of the bisphenol-A by distillation or crystallization. Other procedures are, for example, distillation of the reaction mixture to separate the phenol and bisphenol, or by partial distillation to remove the phenol followed by recrystallization of the residual bisphenol using water, methanol, acetonitrile, methylene chloride or toluene as the solvent.

In order that those skilled in the art will be better able to practice the invention, the following examples are given by way of illustration and not by way of limitation. All parts are by weight.

EXAMPLE 1

The intermediate, N-propyl-3-aminopropanol, was prepared by adding 200 parts of 1-chloro-3-hydroxypropane and 726 parts of N-propylamine to 1600 parts of absolute ethanol. The resulting mixture was heated at reflux for a period of 15 hours. The mixture was than allowed to cool and there was added 127 parts of sodium hydroxide and the reaction mixture was extracted with ether. After drying with magnesium sulfate and removal of the solvent, there was obtained 125.1 parts or a 50% yield of N-propyl-3-amino propanol having a boiling point of 70° C. at 1 torr.

There was added to about 124 parts of the above N-propyl-3-amino propanol dissolved in 1194 parts of chloroform under an atmosphere of nitrogen and at a temperature of about 0° C., 189 parts of thionyl chloride at a rate which was sufficient to maintain the temperature of the resulting reaction mixture below 20° C. When the addition was complete, the solution was brought to reflux for 30 minutes. The reaction mixture was then quenched with excess ethanol and concentrated to provide a yellow viscous oil. There was obtained a quantitative yield of N-propylamino-3-chloro propane hydrochloride after the aforementioned yellow viscous oil was crystallized from ethanol in the form of a white crystalline solid; (M.P. 246°–247° C.).

Twenty parts of the above N-propylamino-3-chloro propane hydrochloride was added to 50 parts of water and the resulting mixture was made basic with a 50% sodium hydroxide solution. The free amine was extracted with chloroform, dried over magnesium sulfate, followed by the removal of the organic solvent which provided a pale yellow oil. The oil was dissolved in 400 parts of absolute ethanol containing 5.0 parts of sodium hydroxide. There was added to this ethanolic solution of the free amine, a solution of 400 parts of ethanol, 3.75 parts of elemental sulfur and 28.1 parts of sodium sulfide nonahydrate which had been refluxed for about a period of 20 minutes. The resulting reaction mixture was then allowed to reflux under an atmosphere of nitrogen. After 15 hours of reflux, the reaction mixture was concentrated on a vacuum evaporator to remove most of the ethanol. The resulting yellow oil was poured into water and the free amino disulfide was extracted with chloroform. The chloroform layer was dried over magnesium sulfate followed by removal of solvent which provided a yellow oil. The yellow oil was then dissolved in ethanol and gaseous hydrogen chloride was bubbled through the solution until the vapors were acidic to moist litmus. Upon cooling, there was obtained a white crystalline solid. The crystalline solid was recrystallized from methanol to provide 14.3 parts or a 72% yield of N-propylamino-3-propane disulfide dihydrochloride having a melting point of 259°–260° C.

The corresponding N-methylamino-2-ethane disulfide and N-methylamino-3-propane disulfide were prepared in accordance with the procedure of T. C. Owen, J. Chem. Soc. (C), 1967, 1373.

A mixture of 1100 parts of anhydrous chloroform, 262.6 parts of Amberlite-118, a crosslinked sulfonated polystyrene polymer manufactured by the Rohm & Haas Company, and 361.1 parts of chlorosulfonic acid was refluxed with stirring under an atmosphere of nitrogen for a period of three days. The mixture was allowed to cool and the chloroform-chlorosulfonic acid solution was decanted from the remaining resin. The resin was then washed with chloroform. The wet resin was then slowly added to a methanol solution at 5° C. at a rate sufficient to maintain the temperature below 15° C. The resulting mixture was filtered and the resin was washed with cold water, methanol, chloroform, and finally diethylether. After a brief air drying, the resin was dried by azeotropic distillation with heptane, followed by drying in an evacuated oven at 70° C.

An ion-exchange catalyst within the scope of the present invention was prepared by refluxing a mixture for 4 hours, of 500 parts of tetrhydrofuran, 40 parts of the above chlorosulfonated resin, 9.47 parts of N-propylamino-3-propane disulfide and about 11.7 parts of triethylamine. The mixture was then allowed to cool and was filtered and washed with saturated sodium bicarbonate solution. The resulting resin was then added to about 500 parts of a 1 normal sodium bicarbonate solution and brought to 90° C. with stirring. The pH of the reaction mixture was continuously maintained at about 9 by the addition of sodium carbonate. After 4 hours, the resin was filtered and washed with water, followed by methanol. There was then added 3.9 parts of triphenylphosphine to about 500 parts of a 90:10 methanol/water solution, followed by addition of the resin. The resulting mixture was then refluxed for 4 hours. There was obtained an ion-exchange catalyst which was filtered and washed with tetrahydrofuran, methanol, water and excess 10% sulfuric acid and water followed by azeotropic drying with toluene. Based on method of preparation and the degree of sulfonation of the starting sulfonated polystyrene, the ion-exchange resin had the following approximate formula,

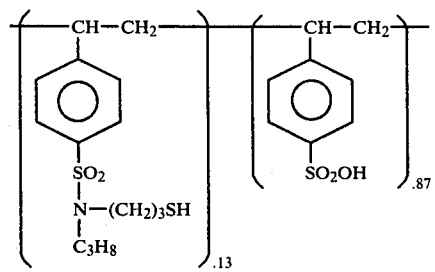

The above procedure was substantially repeated, except that in place of N-propylamino-3-propane disulfide, there was utilized N-methylamino-3-propane disulfide. There was obtained an ion-exchange catalyst having the following approximate formula,

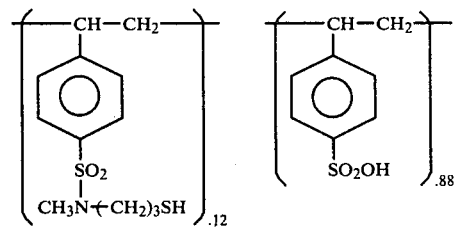

and N-methylamino-2-ethane disulfide which resulted in ion-exchange catalyst having the following formula,

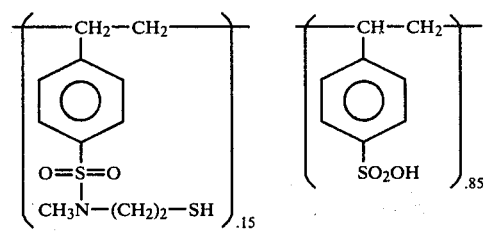

EXAMPLE 2

There was added 1 gram of acetone and 2 grams of ion-exchange catalyst to 10 grams of anhydrous phenol. The resulting mixture was placed in a preheated oil bath at 70° C. and was stirred for a period of 1 hour. The cool solution was then diluted with acetonitrile and examined by high pressure liquid chromatography. The following results were obtained, where "A" under catalyst in Table I below represents catalyst having 13 mole percent of chemically combined N-propylamino propyl mercapto radicals, "B" is ion-exchange catalyst having 12 mole percent of chemically combined N-methylamino propyl mercapto radicals and "C" is ion-exchange catalyst having 15 mole percent of chemically combined N-methylamino ethyl mercapto radicals. "Conversion" means the mole percent of bisphenol actually formed divided by the possible theoretical amount of bisphenol which could be formed based on the weight of acetone used:

TABLE I

| Catalyst | % Conversion |
|---|---|
| A | 43 |
| B | 65 |
| C | 79.4 |

The above results show that the ion-exchange resins having methyl-substituted amino mercapto radicals are more effective as an ion-exchange catalyst than the ion-exchange resin having propyl-substituted amino mercapto radicals in the phenol-acetone reaction.

It was further found that 2 parts of an ion-exchange resin prepared in accordance with copending application Ser. No. 103,095 with ethyl aminodisulfide having about 87 mole percent of a mixture of styrene units and sulfonated styrene units chemically combined with about 13 mole percent of sulfonated styrene units having chemically combined aminoethyl mercaptan group covalently attached to sulfur, provided a conversion of about 66.8% when heated with a mixture of 1 part of acetone and 10 parts of phenol at 70° C. for 1 hour. This can be compared to a conversion of about 40% with 2 parts of an ion-exchange resin produced by neutralizing the sulfonated polystyrene with 2-mercaptoethylamine as shown by McNutt et al U.S. Pat. No. 3,394,089.

EXAMPLE 3

Bisphenol-A was prepared in a continuous manner over a 10 day period by feeding 8:1 molar amounts of phenol and acetone to a column at a temperature of about 70° C. which contained an ion-exchange bed consisting of a sulfonated polystyrene substituted with 13 mole % of N-propyl amino-3-propyl mercapto radicals. The results of the 10 day study are shown in Table II below, where "% Conversion" is as defined in Example 2 and "% Latent BPA" indicates isomeric reaction products which form p,p'-BPA upon isomerization.

TABLE II

| Day # | % Conversion | % p,p-BPA | % Latent BPA | % Other Isomers |
|---|---|---|---|---|
| 1 | 66.4 | 95.4 | 4.3 | 0.31 |
| 2 | 64.6 | 95.6 | 4.2 | 0.38 |
| 3 | 53.1 | 95.8 | 4.2 | 0.10 |
| 4 | 62.6 | 96.1 | 3.4 | 0.53 |
| 5 | 67.8 | 96.0 | 4.0 | 0.26 |
| 6 | 71.7 | 95.5 | 4.3 | 0.25 |
| 7 | 58.9 | 95.6 | 4.2 | 0.29 |
| 9 | 58.3 | 95.4 | 4.4 | 0.23 |
| 10 | 64.1 | 94.7 | 4.87 | 0.30 |

The stability of the catalyst in this experiment is demonstrated by the observation of normal percent conversion on the 10th day which followed treatment of the catalyst by a typical acid regeneration with 1.0 N $H_2SO_4$ on the 9th day. It was further found that an attempt to regenerate the ion-exchange catalyst of McNutt et al described in Example 2 after an equivalent reaction period resulted in the destruction of the catalyst due to acid hydrolysis.

Although exhibiting superior stability to acid hydrolysis as compared to the ion-exchange catalyst of McNutt et al, U.S. Pat. No. 3,394,089, the ion-exchange catalyst of Ser. No. 103,095 was found to result in a decrease in percent conversion of p,p'-bisphenol-A and an increase in percent, o,p'-bisphenol-a when used under continuous conditions as described above.

EXAMPLE 4

There was added 22 grams of N-propylamino-3-propane disulfide dihydrochloride, 8.8 grams of KOH and 80 grams of sodium bicarbonate to 800 ml of an aqueous methanol solution containing 10% by weight methanol. The resulting solution was allowed to stir at ambient temperatures for 20 minutes. There was then added to the solution, 80 grams of polystyrene having 335 milliequivalents of chemically combined sulfonyl chloride and the resulting reaction mixture was stirred at reflux for 4 hours. There was then added to the resulting mixture 40 grams of sodium carbonate and the mixture was heated for an additional hour.

After the mixture was allowed to cool it was filtered. The resulting resin was washed with water followed by methanol. The resin was then added to 800 ml of an aqueous methanol solution having 10% water containing 15.9 grams of tri-n-butylphosphine. The resulting mixture was heated at reflux for 6 hours. The mixture was then filtered and the solids were washed with methanol, acetone, water and a 10% aqueous sulfuric acid solution, followed with additional washing with water. Water was then azeotropically removed from the resulting resin with toluene. The resin was then dried in an evacuated drying oven to remove residual amounts of toluene. Based on method of preparation and elemental analysis for chemically combined nitrogen, there was obtained, assuming a molar equivalence of mercaptan to nitrogen and a starting chloro sulfonated polystyrene substantially free of chemically combined unsulfonated styrene units, an ion-exchange catalyst having the following approximate formula,

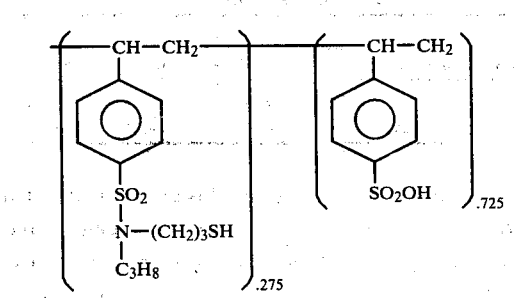

In accordance with the procedure of example 2, the above ion-exchange catalyst provided a 72% conversion of bisphenol-A, based on the possible theoretical amount which could be formed based on the weight of acetone used.

Although the above examples are directed to only a few of the very many variables of the ion-exchange resins of the present invention and method for making, it should be understood that the present invention is directed to a much broader variety of ion-exchange resins based on the use of amino organodisulfides of formula (1) and on the polymer shown in the description preceding these examples.

What I claim as new and desire to secure by Letters Patent of the United States is:

1. An ion-exchange resin comprising a sulfonated aromatic organic polymer having chemically combined sulfonated aromatic organic units with N-alkylaminoorganomercaptan groups attached to the sulfonyl radicals by covalent nitrogen-sulfur linkages.

2. An ion-exchange resin comprising a blend of sulfonated aromatic organic polymer having chemically combined sulfonated aromatic organic units with N-alkylaminoorganomercaptan group attached to sulfonyl radicals by covalent nitrogen-sulfur linkages, and sulfonated aromatic organic polymer free of sulfonyl radicals having N-alkylaminoorganomercaptan groups attached thereto.

3. An ion-exchange resin in accordance with claim 1, where the sulfonated aromatic organic polymer consists essentially of styrene units substituted with sulfonyl radicals having N-alkylaminopropylmercaptan groups attached to sulfur by covalent nitrogen-sulfur linkaged chemically combined with styrene units substituted with —SO₃H radicals.

4. An ion-exchange resin in accordance with claim 1, where the sulfonated aromatic organic polymer consists essentially of styrene units substituted with sulfonyl radicals having N-alkylaminoethylmercapto groups attached to sulfur by covalent nitrogen-sulfur linkages chemically combined with styrene units substituted with —SO₃H radicals.

5. An ion-exchange resin in accordance with claim 1, where the sulfonated aromatic organic polymer consists essentially of styrene units substituted with sulfonyl radicals having N-propylaminopropylmercapto groups attached to sulfur by covalent nitrogen-sulfur linkages chemically combined with styrene units substituted with —SO₃H radicals.

6. A method for making bisphenol which comprises reacting a ketone and a phenol in the presence of an effective amount of a cation-exchange resin having from about 5–40 mole percent of chemically combined aromatic sulfonyl units with an N-alkyl aminoorganomercapto radical of the formula,

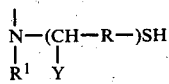

covalently bonded to sulfur by nitrogen-sulfur linkages, where R is a divalent $C_{(1-13)}$ organo radical, $R^1$ is a $C_{(1-8)}$ monovalent alkyl radical and Y is a member selected from hydrogen, carboxy and nitrile.

7. A method in accordance with claim 6, where the bisphenol is bisphenol-A.

8. A method in accordance with claim 6, where the N-alkylaminoorganomercapto radical is N-propylaminopropylmercapton.

* * * * *

UNITED STATES PATENT AND TRADEMARK OFFICE
Certificate

Patent No. 4,396,728                                Patented August 2, 1983

Gary R. Faler

Application having been made by Gary R. Faler, the inventor named in the patent above identified, and General Electric Co., the assignee, for the issuance of a certificate under the provisions of Title 35, Section 256, of the United States Code, adding the name of George R. Loucks as a joint inventor, and a showing and proof of facts satisfying the requirements of the said section having been submitted, it is this 22nd day of May, 1984, certified that the name of the said George R. Loucks is hereby added to the said patent as a joint inventor with the said Gary R. Faler.

Fred W. Sherling,
*Associate Solicitor.*